US008706187B2

(12) United States Patent
Kucharczyk et al.

(10) Patent No.: US 8,706,187 B2
(45) Date of Patent: Apr. 22, 2014

(54) IMAGING METHODS FOR EARLY DETECTION OF BRAIN TUMORS FOLLOWING EMBRYONIC STEM CELL IMPLANTS

(75) Inventors: John Kucharczyk, Reno, NV (US); Michael E. Moseley, Redwood City, CA (US)

(73) Assignee: The Regents of the University of Minnesota, Minneapolis, MN (US)

( * ) Notice: Subject to any disclaimer, the term of this patent is extended or adjusted under 35 U.S.C. 154(b) by 2392 days.

(21) Appl. No.: 11/386,394

(22) Filed: Mar. 22, 2006

(65) Prior Publication Data

US 2006/0239920 A1 Oct. 26, 2006

Related U.S. Application Data

(63) Continuation-in-part of application No. 09/606,137, filed on Jun. 28, 2000.

(51) Int. Cl.
*A61B 5/055* (2006.01)
(52) U.S. Cl.
USPC .......................................... 600/410; 600/420
(58) Field of Classification Search
None
See application file for complete search history.

(56) References Cited

U.S. PATENT DOCUMENTS

| 5,190,744 | A | 3/1993 | Rocklage et al. | 424/9.34 |
|---|---|---|---|---|
| 5,487,739 | A | 1/1996 | Aebischer et al. | 604/890.1 |
| 5,494,655 | A | 2/1996 | Rocklage et al. | 424/9.36 |
| 5,833,947 | A | 11/1998 | Rocklage et al. | 424/9.36 |
| 5,869,463 | A * | 2/1999 | Major et al. | 514/44 |
| 5,910,112 | A * | 6/1999 | Judd et al. | 600/410 |
| 5,951,473 | A * | 9/1999 | Sherry et al. | 600/420 |
| 5,980,885 | A * | 11/1999 | Weiss et al. | 424/93.21 |
| 6,026,316 | A | 2/2000 | Kucharczyk et al. | 600/420 |
| 6,061,587 | A | 5/2000 | Kucharczyk et al. | 600/411 |
| 6,112,112 | A | 8/2000 | Gilhuijs et al. | 600/425 |
| 6,310,477 | B1 | 10/2001 | Schneider | 324/307 |
| 6,315,981 | B1 | 11/2001 | Unger | 424/9.323 |
| 6,319,682 | B1 | 11/2001 | Hochman | 435/29 |
| 6,491,894 | B1 | 12/2002 | Ruoslahti et al. | 424/9.1 |
| 6,497,872 | B1 | 12/2002 | Weiss et al. | 424/93.1 |
| 6,503,478 | B2 | 1/2003 | Chaiken et al. | 424/9.1 |
| 6,521,210 | B2 | 2/2003 | Ohkawa | 424/9.3 |
| 6,537,232 | B1 | 3/2003 | Kucharczyk et al. | 600/561 |
| 6,599,274 | B1 | 7/2003 | Kucharczyk et al. | 604/264 |
| 6,626,902 | B1 | 9/2003 | Kucharczyk et al. | 604/41 |
| 6,749,833 | B2 | 6/2004 | Raghavan et al. | 424/9.1 |

OTHER PUBLICATIONS

1993: Howe F A; Maxwell R J; Saunders D E; Brown M M; Griffiths J R Proton spectroscopy in vivo. Magnetic resonance quarterly 1993;9(1):31-59.*

(Continued)

*Primary Examiner* — Long V. Le
*Assistant Examiner* — Colin T Sakamoto
(74) *Attorney, Agent, or Firm* — Mark A. Litman & Associates, P.A.

(57) ABSTRACT

Non-invasive imaging methods and minimally invasive sensing methods are used for assessing the viability of cells implanted in the central nervous system for therapeutic purposes and for detecting the transformation of such cells, including embryonic stem cells, into brain tumors. In particular, the present invention provides an imaging means for differentiating normal cell proliferation and angiogenesis following a cell implant from abnormal tumor growth and neovascularization associated with teratoma-inducing implanted embryonic stem cells.

12 Claims, 13 Drawing Sheets

(56) References Cited

OTHER PUBLICATIONS

Bell JD; Bhakoo KK. (Nov 1998). Metabolic changes underlying 31P MR spectral alterations in human hepatic tumours. NMR Biomed. 11:354-359.*

Bhujwalla ZM, Shungu DC, He Q, Wehrle JP and Glickson JD (1994) MR studies of tumors: relationship between blood flow, metabolism and physiology. In: NMR in Physiology and Biomedicine. Gillies RJ (ed), pp. 311-328, Academic Press: San Diego.*

Howe F A; Maxwell R J; Saunders D E; Brown M M; Griffiths J R Proton spectroscopy in vivo. Magnetic resonance quarterly 1993;9(1):31-59.*

U.S. Appl. No. 09/606,137, filed Jun. 28, 2000. Moseley, et al.

U.S. Appl. No. 10/444,884, filed May 23, 2003. Kucharczyk, et al.

Bjorklund, A. "Neurobiology—Better Cells for Brain Repair," Nature 363 (6419) 414-415 (Apr. 1993).

Allison, S.W., et al., "Positive Pressure Infusion of Fluorescent Nanoparticles as a Probe of the Structure of Brain Phantom Gelatins," Nanotechnology, 13(4), 484-486, (Aug 2002).

Allison, S.W., et al., "Nanoscale Thermometry via the Fluorescence of YAG:Ce Phosphor Particles: Measurements from 7 to 77° C, "Nanotechnology, 14(8), 859-863, (Aug 2003).

Howe, F.A., et al., "Proton Spectroscopy in-vivo," Magnetic Resonance Quarterly, 9(1), 31-59, (Mar. 1993).

Folkman, J., et al., "Angiogenic Factors," Science, 235(4787), 442-447, (Jan. 23, 1987).

Jain, R.K., "Determinants of Tumor Blood Flow—a Review," Cancer Research, 48(10), 2641-2658, (May 15, 1988).

Thomlinson, R.H., et al., British Journal of Cancer, 9, 539-549, (1955).

Falk, P., "Differences in Vascular Pattern between the Spontaneous and the Transplanted C3H Mouse Mammary-Carcinoma," European Journal of Cancer & Clinical Oncology, 18(2), 155-165, 1982.

Less, J.R., et al., "Interstitial Hypertension of Human Tumors," Cancer Research, 52(22), 6371-6374, (Nov. 15, 1992).

Jirtle, R.L., "Chemical Modification of Tumor Blood Flow," International Journal of Hyperthermia, 4(4), 355-371, (Jul.-Aug. 1998).

Stokes, B.T., et al., "Oxygen-Transport in Intraspinal Fetal Grafts—Graft Host Relations," Experimental Neurology, 111(3), 312-323 Mar. 1991.

Wein, L.M., et al., "Dynamic Optimization of a Linear Quadratic Model with Imcomplete Repair and Volume-Dependent Sensitivity and Repopulation," International Journal of Rediation Oncology and Biological Physics, 47(4), 1073-1083, (2000).

Reddy, R., et al., "$^{17}$O-Decoupled $^{1}$H Detection Using a Double-Tuned coil," Magnetic Resonance Imaging, 14(9), 1073-1078, (1996).

Ronen, I., et al., "A New Method for Proton Detection of ($H_2O$)-$^{17}$O with Potential Applications to Functional MRI," MagneticResonance in Medicine, 32(6), 789-793, (Dec. 1994).

Hopkins, A. L., et al., "Improved Sensitivity of Proton MR to $^{17}$O as a Contrast Agent Using Fast Imaging—Detection in Brain," Magnetic Resonance in Medicine, 7(2), 222-229, (Jun. 1988).

Bell, J. D., et al., "Metabolic changes underlying $^{31}$P MR spectral alterations in human hepatic tumours," NMR in Biomed, 11: 354-359, (1998).

Maintz, David, et al., "Phosphorus-31 MR spectroscopy of normal adult human brain and brain tumours," NMR Biomed, 15: 18-27 (2002).

Gillies, Robert J., et al., "In Vivo Magnetic Resonance Spectroscopy in Cancer," Annu. Rev. Biomed. Eng. 7: 287-326 (2005).

Kwong, K. K., et al., "Proton NMR Imaging of Cerebral Blood-flow Using ($H_2O$)-O-17," Magnetic Resonance in Medicine, 22(1), 154-158, (Nov. 1991).

Abstract of Negendank, W., "Studies of Human Tumors by MRS—A Review," NMR in Biomedicine 5(5), 303-324, (Sep.- Oct. 1992).

Abstract of Watts, C., et al., "The Development of Intracerebral Cell-Suspension Implants is Influenced by the Grafting Medium," Cell Transplantation, 7(6), 573-583, (Nov.- Dec. 1998).

* cited by examiner

Flow chart of MR Visualization of Implanted Stem Cells

Bolus contrast injection to measure blood volume and capillary density

Capillary Density and Measured Blood Volume

Capillary density is derived from % blood volume and Specific density of tissue

Use Of O-17 Gas And Water To Measure Local Tissue/Tumor Metabolism/Flow

Use Of Measured Diffusion MR ADC To Identify Implant/Teratoma/Necrosis/CSF

Measured ADC and Cell Classification:
ADC of normal brain = 0.8- 1.0 x $10^{-3}$ mm$^2$/s
ADC of normal cell implant = 0.9- 1.2 x 10-3 mm$^2$/s
ADC of tumor/teratoma = 1 – 2 x 10-3 mm$^2$/s
ADC of edema/necrosis = 2 – 3 x 10-3 mm$^2$/s
ADC of CSF = 3-5 x 10-3 mm$^2$/s Fe-labeled Cells Follow Signals Along White Matter Diffusion Tensors

Fe-labeled Cells Follow Signals Along White Matter Diffusion Tensors

Path of Fe-labeled cells following signalling apparent
from T2 or T2*-weighted MRI as decrease in tissue
T2*, as decrease in tensor signal, or as increase in
local averaged ADC (less tensor effects).

Flow chart of MR Spectroscopy for Local Metabolic Viability

"Normal" tissue/cell metabolism:
normal metabolites + low lactate

MR Spectroscopy Imaging for Local Metabolic Viability

MR Spectroscopic Maps

Segmented H-1 water image

Low-pass water image

N-acetyl image

Creatine image

Choline image

Local Metabolic Viability and Metabolic Levels from MRS

IMAGING METHODS FOR EARLY DETECTION OF BRAIN TUMORS FOLLOWING EMBRYONIC STEM CELL IMPLANTS

RELATED APPLICATION DATA

This application is a continuation-in-part application of U.S. patent Ser. No. 09/606,137 filed Jun. 28, 2000 and claims the priority date of the earlier application.

BACKGROUND OF THE INVENTION

1. Field of the Invention

This invention relates to non-invasive imaging methods and minimally invasive sensing methods for assessing the viability of implanted stem cells and for the early detection of the transformation of implanted stem cells into brain tumors.

2. Background of the Art

Studies have demonstrated that the symptoms of Parkinson's disease (PD) can be improved by transplanting dopaminergic (DA) stem cells into the brain of PD patients. A major obstacle to effective stem cell therapy of PD is that only a low percentage of cells implanted into the brain survive more than seven days (Bjorklund, A., "Neurobiology—Better Cells for Brain Repair," Nature 363(6419), 414-415, (Apr. 1, 1993)). Many factors have been shown to influence long-term viability of DA stem cell implants, including the site of the implant, the specificity of donor tissue, and the techniques used in the preparation of the cells to be implanted. One potential factor which may account for the high attrition rate of implanted stem cells is a lack of nutritive support. Angiogenesis in cell implants has been shown to occur after approximately three days post-implantation, which suggests that most implanted cells die within the first 48 to 72 hours after implantation when they are dependent on local diffusion for oxygen and glucose; see, for example, Watts, C., et al., "The Development of Intracerebral Cell-Suspension Implants is Influenced by the Grafting Medium," Cell Transplantation, 7(6), 573-583, (November-December 1998). The precise mechanism of survival of implanted cells until a vascular supply becomes established is not known, although it may be influenced by the oxygen tension of the local environment during the course of graft vascularization; see, for example, Stokes, B. T., et al., "Oxygen-Transport in Intraspinal Fetal Grafts—Graft Host Relations," Experimental Neurology, 111(3), 312-323, (March 1991).

A method to monitor non-invasively the ongoing viability of the cell implant is needed, in particular to determine whether the cells are adequately perfused by the local microvasculature. U.S. Pat. No. 5,190,744 to Rocklage et al. discloses MRI methods for evaluating local and regional tissue perfusion based on first-pass tracking of a bolus of MRI contrast agent. U.S. Pat. No. 5,494,655 to Rocklage et al. additionally discloses MRI methods for evaluating local and regional tissue perfusion changes induced by administration of a vasodilatory or vasoconstrictive drug agent. U.S. Pat. No. 5,833,947 to Rocklage et al. further discloses MRI methods for evaluating local and regional tissue perfusion changes induced by surgical procedures, such as cell implants. U.S. patent application. Ser. No. 09/606,137, co-authored by two of the present authors, discloses methods for indicating viability of transplanted progenitor or stem cells based on imaging measurements of changes in blood flow in the region of the cell implant. Unlike the present invention, however, none of these patents disclose a method for quantitating the functional capillary density in the anatomic region of the cell implant, or for quantitatively determining the metabolic status of a population of living cells implanted into a tissue in a human body.

The clinical utility of cell therapy is further limited by the fact that the incidence of teratoma tumor formation from implanted embryonic stem cells remains high despite significant recent advances in implant methodology. Magnetic resonance (MR) methods have been used to investigate the relationship of tumor metabolism to blood flow and oxygenation, proliferation, and differentiation. Several reviews published in the medical literature have summarized the morphological, metabolic, and physiological characteristics of tumors and their relationship to $^{1}H$, $^{13}C$, and $^{31}P$ measurements obtained by MR spectroscopy; see for example Wehrle, J. P., et al., "$^{31}P$ NMR-Spectroscopy of Tumors in vivo," Cancer Biochemistry Biophysics, 8(3), 157-166, (1986) and Howe, F. A., et al., "Proton Spectroscopy in-vivo," Magnetic Resonance Quarterly, 9(1), 31-59, (March 1993).

Tumor growth to a volume of about 1 cubic mm can occur without contiguous microvascular support, since all the essential nutrients and waste products can diffuse across this distance. However, blood vessels are essential for further tumor progression. Inadequate local blood flow and low concentrations of glucose and oxygen appear to influence the latency of expression of DNA damage. Blood flow also controls cellular environment and heat clearance, factors which are important in hyperthermic treatment of tumors. The sensitivity of cells to radiation depends significantly on the concentration of cellular oxygen. A non-invasive imaging method of monitoring blood flow and oxygenation during the post-transplant period, in conjunction with methods to modify these parameters, would increase the effectiveness of early detection of tumors and potentially improve treatment strategies during the early stages of tumor development following embryonic stem cell implants.

Tumor vascular supply is derived from normal vessels incorporated from the host tissue and new blood vessels stimulated by tumor angiogenesis factors; see Folkman, J., et al., "Angiogenic Factors," Science, 235(4787), 442-447, (Jan. 23, 1987). Neovascular development is characterized by various structural abnormalities, including an absence of smooth muscle cells, collapsed vessels due to increased tissue pressure, stasis, large sinusoidal structures, arteriovenous shunts, and thrombosis; see Jain, R. K., "Determinants of Tumor Blood Flow—a Review," Cancer Research, 48(10), 2641-2658, (May 15, 1988).

If neovascularization associated with new tumors cannot match the rapid proliferation of tumor cells, the result is a reduced and inhomogeneous supply of blood, substrates, and oxygen leading to hypoxia, anoxia, and ultimately cell death. Surviving cells generally are located at distances of 150 microns or less from the nearest blood vessel; see Thomlinson, R. H., et al., British Journal of Cancer, 9, 539-549, (1955). However, cellular debris, fatty acids, proteins, and nucleic acid fragments present in necrotic areas can also interfere with mitochondrial functioning of cells in adjacent perfused areas; see Falk, P., "Differences in Vascular Pattern between the Spontaneous and the Transplanted C3H Mouse Mammary-Carcinoma," European Journal of Cancer & Clinical Oncology, 18(2), 155-165, 1982. The composition of tumor interstitial fluid is similar to normal interstitial fluid, except for high concentrations of lactate (10-30 mM), and a very low content of free glucose (0-2 mM). Tumors also have elevated interstitial pressure, which has been attributed to the absence of functioning lymphatics, the high filtration coefficient and vascular permeability of tumor blood vessels, and the rapid proliferation of cells in confined spaces; see Less, J.

R., et al., "Interstitial Hypertension in Human Tumors. 4. Interstitial Hypertension in Human Breast and Colorectal Tumors," Cancer Research, 52(22), 6371-6374, (Nov. 15, 1992).

By comparison with other methods, MR is capable of measuring blood flow and oxygenation non-invasively, either indirectly by evaluating metabolism or by using contrast agents. $^1$H MR spectra of brain tumors show increased lactate and total choline and reduced N-acetyl aspartate (NAA) levels compared to normal brain spectra; see Negendank, W., "Studies of Human Tumors by MRS—A Review," NMR in Biomedicine, 5(5), 303-324, (September-October 1992). The high levels of lactate are consistent with high glycolytic rates and poor blood flow associated with tumors. The high levels of total choline may be due to increased membrane degradation or turnover, since the choline compounds observed in $^1$H MR spectra are both membrane precursors and breakdown products. Hypoxia is known to result in membrane breakdown and the release of free fatty acids.

Compared to other brain tumors, teratomas almost always exhibit calcific, lipomatous, or cystic foci, making their MRI diagnosis relatively easy. For example, the high signal intensity of a teratoma on a T1-weighted (TR 600/TE 24 ms) sequence is suggestive of fat, an impression that can be verified by the loss of signal intensity over two echoes of a long TR sequence. A cystic focus in a teratoma exhibits a chemical shift artifact which can be readily appreciated on MR imaging. While the prior art discloses imaging methods for detecting and diagnosing diseases of the central nervous system, including brain tumors, imaging methods which provide for early detection of teratomas that originate from implanted stem cells have not been previously disclosed.

U.S. Pat. No. 6,319,682 to Hochman discloses optical detection techniques for the assessment of physiologic state and metabolic viability of biological materials, including cells. An express purpose of the Hochman patent is high throughput screening of candidate agents and conditions to evaluate their suitability as diagnostic or therapeutic agents. However, unlike the present invention, Hochman does not disclose a method means for assessing the metabolic viability of implanted stem cells and for the early detection of their transformation into teratomas.

U.S. Pat. No. 6,497,872 to Weiss et al. discloses methods of transplanting multipotent neural stem cell progeny to a host by obtaining a population of cells derived from mammalian neural tissue containing at least one multipotent neural stem cell; culturing the neural stem cell in a culture medium containing one or more growth factors which induce multipotent neural stem cell proliferation; inducing proliferation of the multipotent neural stem cell to produce neural stem cell progeny; and transplanting the multipotent neural stem cell progeny to the host. Also provided in the patent to Weiss et al. are methods of transplanting neural stem cell progeny to a host by obtaining an in vitro cell culture containing CNS neural stem cells and transplanting the stem cells into the host.

U.S. Pat. No. 6,503,478 to Chaiken et al. discloses methods and materials for obtaining spatially resolved images of specific types of tissues. The method for imaging tissue comprises administering to the tissue a deuterated imaging agent and performing spectroscopy. Electromagnetic radiation, such as a near infrared laser beam, is directed to a tissue of interest. When used in combination with a light collection system, it is possible to map out a specific volume of tissue, obtaining information regarding the distribution of specific endogenous chemical species. In some embodiments disclosed by Chaiken et al., specific imaging agents are employed to impart contrast between chemically different types of tissues.

U.S. Pat. No. 6,521,210 to Ohkawa discloses a method for imaging a malignancy in a patient, in situ, but requires feeding the patient a nutrient that is enriched with the isotope $^{13}$C. MRI techniques are then used on the patient with rf energy that is tuned to the nuclear resonance of $^{13}$C. An image of selected tissue in the patient is thereby created, and is evaluated for any concentrations of $^{13}$C that will delineate a malignancy. A subsequent MRI procedure may be performed to determine the efficacy of any intervening treatment, or to determine a growth rate for the malignancy However, unlike the present invention, the prior art does not disclose a method for assessing the metabolic activity and perfusion status of implanted stem cells as a practical and reliable MR imaging means for early detection of the transformation of implanted cells into brain tumors.

SUMMARY OF THE INVENTION

The present invention provides an MR imaging method to monitor the metabolic status of transplanted cells and their assimilation into a tissue transplant environment based on MR indicators of normal and abnormal cell growth and proliferation. According to the invention, metabolic changes arising from cell replication can be measured using localized proton lactate and metabolite signals, and the resulting MR data provide a non-invasive assessment of normal cell viability. In one preferred embodiment, the metabolic changes are measured by MR using non-invasive in vivo proton spectroscopy with local or volume RF-coils. In a particularly preferred embodiment, proton observable metabolites GABA, PCr, creatine, choline, and lactate are measured. According to the invention, viable cell implants can be distinguished from abnormal cells and brain tumors based on quantitative regional levels of lactate and other metabolites.

In another embodiment of the present invention, a quantitative assessment of the populations of living to dead cells is obtained from the molar ratios of the proton signals of lactate to metabolites. In a particularly preferred embodiment of the invention, local glucose turnover is monitored by non-invasive in vivo $^{13}$C labeled glucose introduced directly into brain tissues together with the cell implant. Glucose metabolism in the cell implant is assessed by observing the in vivo conversion of the $^{13}$C labeled glucose into $^{13}$C labeled metabolic by-products. According to the invention, the levels and turnover rates of glucose utilization, as measured by the concentrations of the converted compounds, reflect the ongoing viability of the cell implant. This can be both qualitatively and quantitatively assessed by the technology practices described herein.

In another embodiment of the invention, the viability of the cell implant is also assessed by measuring localized phosphorous high-energy metabolite concentrations by non-invasive in vivo $^{31}$P MR spectroscopy. Regional concentrations of the $^{31}$P containing metabolites of ATP, ADP, PCr are acquired along with inorganic phosphates, as well as fructose and glucose-6-phosphates. According to the invention, ATP and PCr levels in living and metabolically active cells are significantly different from dead or dying cells, which will contain larger than normal levels of inorganic phosphates, and will display an abnormal intracellular pH, measured as the chemical shift differences between PCr and the inorganic phosphate $^{31}$P signals.

In another embodiment of the present invention, cell viability is evaluated by measuring the alterations in tissue sodium measured by $^{23}$Na MRI. According to the invention, intracellular sodium levels are distinguished from extracellular sodium levels using chemical shift differences from chemical shift reagents introduced to separate extracellular sodium from intracellular sodium. Only extracellular sodium is shifted by these reagents. In another preferred embodiment of the present invention, cell viability is also evaluated by assessing the intra- and extracellular sodium based on the T1 and T2 relaxation times of the two constituents.

The present invention also provides a method to identify early tumor formation through quantification of the relationship between the predicted size (number of cells) of the tumor, acute changes in tumor blood flow induced by administration of vasoactive drug agents, and the resulting $^1$H MR spectra. In the method of the invention, the vasodilator hydralazine is used to reduce tumor blood flow in transplanted tumors based on the "steal" phenomenon; see Jirtle, R. L., "Chemical Modification of Tumor Blood Flow," International Journal of Hyperthermia, 4(4), 355-371 (July-August 1988). The decrease in systemic blood pressure and the vasodilatory action of hydralazine on the arteriolar smooth muscle cells, present in normal tissue vasculature, but absent in poorly differentiated tumor vasculature, results in near vascular collapse within the tumor. $^1$H MR spectra obtained following administration of hydralazine will show a predictable increase in the lactate peak in the tumor area related to tumor size (number of tumor cells) with no changes in total choline or creatine. These changes are consistent with the glycolytic metabolism of glucose to lactate to maintain energy levels in the absence of oxygen. Thus, the present invention provides an imaging means for distinguishing between normal cell proliferation and angiogenesis following a cell implant versus abnormal tumor growth and neovascularization associated with teratoma-inducing implanted cells.

Further in the method of the invention, nicotinamide, or other similar vasoactive drug agent, is used to preferentially increase tumor blood flow and oxygenation and thereby further distinguish between normal angiogenesis and neovascularization associated with tumor cells formed from implanted stem cells. Nicotinamide has been shown to significantly decrease total choline peak (mainly phosphocholine and glycerophosphocholine) with no significant changes in the lactate peak. Since tumor cells are capable of aerobic glycolysis, an increase in blood flow induced by nicotinamide administration will concurrently improve lactate clearance while increasing lactate formation due to increased glucose supply.

In a further embodiment, the method of the present invention provides a non-invasive imaging means of quantifying the degree of necrosis in tumors associated with implanted cells. In the method of the invention, necrotic areas can be detected and their volume based on their low signal intensity on T2-weighted spin-echo images resulting from extravasation of red blood corpuscles and stasis in necrotic areas.

According to the methods of the invention, these MR changes can be detected by a volume coil surrounding the tissue or by introduction of a local multi-tuned MRI RF-coil arrangement. The local MR coil can be attached to the local infusion catheter. This can also be connected to local pH meters, glucose and other meters or monitors, local gas sensors, video monitors, optical detectors, and chemical and other sensors.

In another embodiment of the invention, local tissue blood flow is monitored by MR perfusion imaging following infusion of T1- or T2*-shortening agents, including especially MR-visible paramagnetic, superparamagnetic, or non-magnetic contrast agents.

In a particularly preferred embodiment, local blood flow is measured in the cell implant by the local introduction of hyperpolarized Xenon gas (by Xe-tuned MRI RF coils). The elimination of the Xe and the decay of the Xe signal is a measure of the local blood flow from that region.

In another embodiment of the invention, local blood flow is measured through the use of optically-active dyes and coloring agents by monitoring the concentration-time changes by an optical probe. The decay of the optical agent or optical signal as local blood flow carries the agent or compound from the cell implant.

It is one aspect of the present invention to provide an imaging means for quantitating the number of living cells implanted into a tissue in a human body.

A second aspect of the present invention is to provide an MR imaging method for quantitatively determining the apparent diffusion coefficient in a population of living cells implanted into a tissue in a human body.

A third aspect of this invention is to provide an MR method for quantitatively determining the pH and fluid-electrolyte parameters in a population of living cells implanted into a tissue in a human body.

A fourth aspect of the invention is to provide an MR method for quantitatively determining the phosphorus and water proton metabolites in a population of living cells implanted into a tissue in a human body.

A fifth aspect of the present invention is to provide an MR imaging means for quantitating the functional capillary density of the tissue region contiguous with the cell implant.

A sixth aspect of this invention to provide automated computer software methods for modeling and monitoring cell implant therapy, specifically for data collection related to monitoring cell viability and early teratoma formation following cell implants.

As noted herein, these techniques can be used both qualitatively and quantitatively to asses the state of cells in the patient, with certain of the techniques being less exact in quantitative capability than others.

DETAILED DESCRIPTION OF THE INVENTION

Figure 1A:
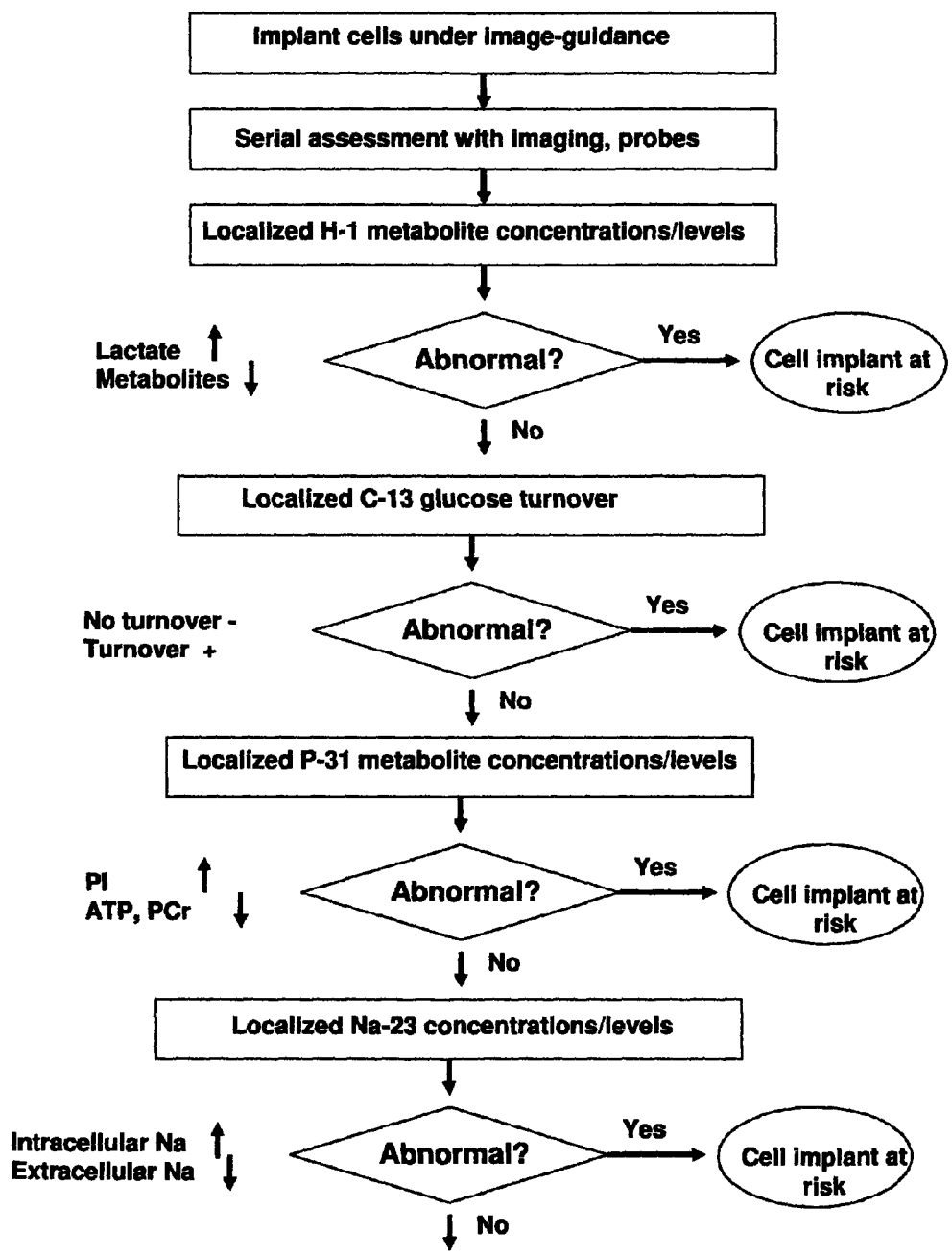
FIG. 1A is a flowchart for MRI visualization of implanted stem cells according to the present invention.
Figure 1B:
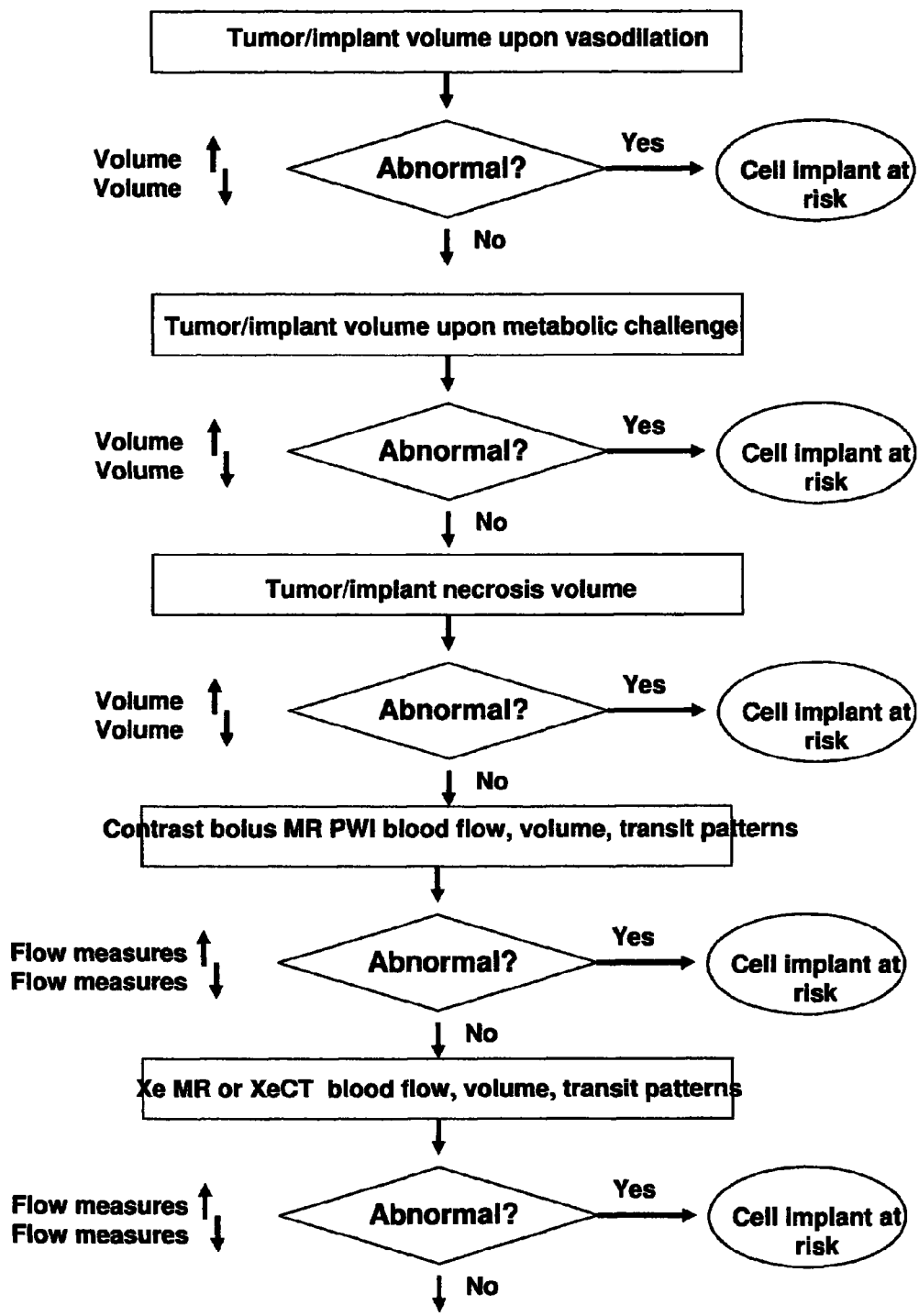
FIG. 1B is a flowchart for MRI visualization of implanted stem cells according to the present invention.
Figure 1C:
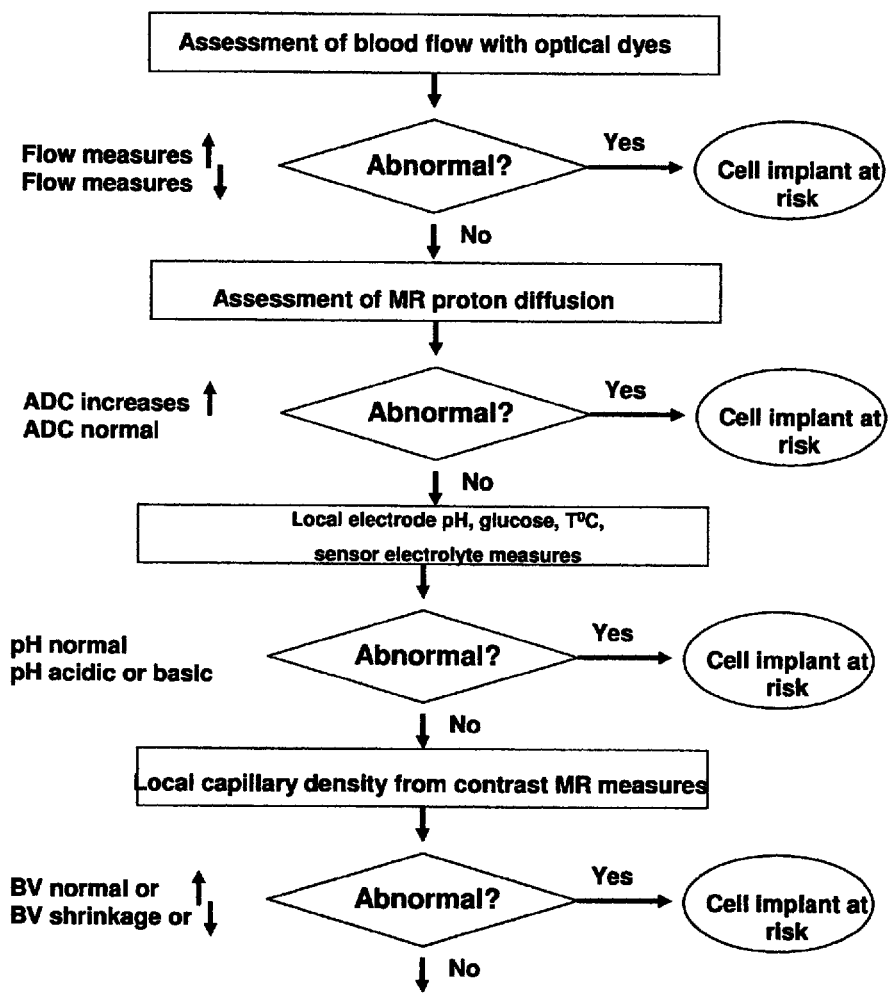
FIG. 1C is a flowchart for MRI visualization of Border Evaluation of turner/implant shape or extent according to the present invention.
Figure 1D:
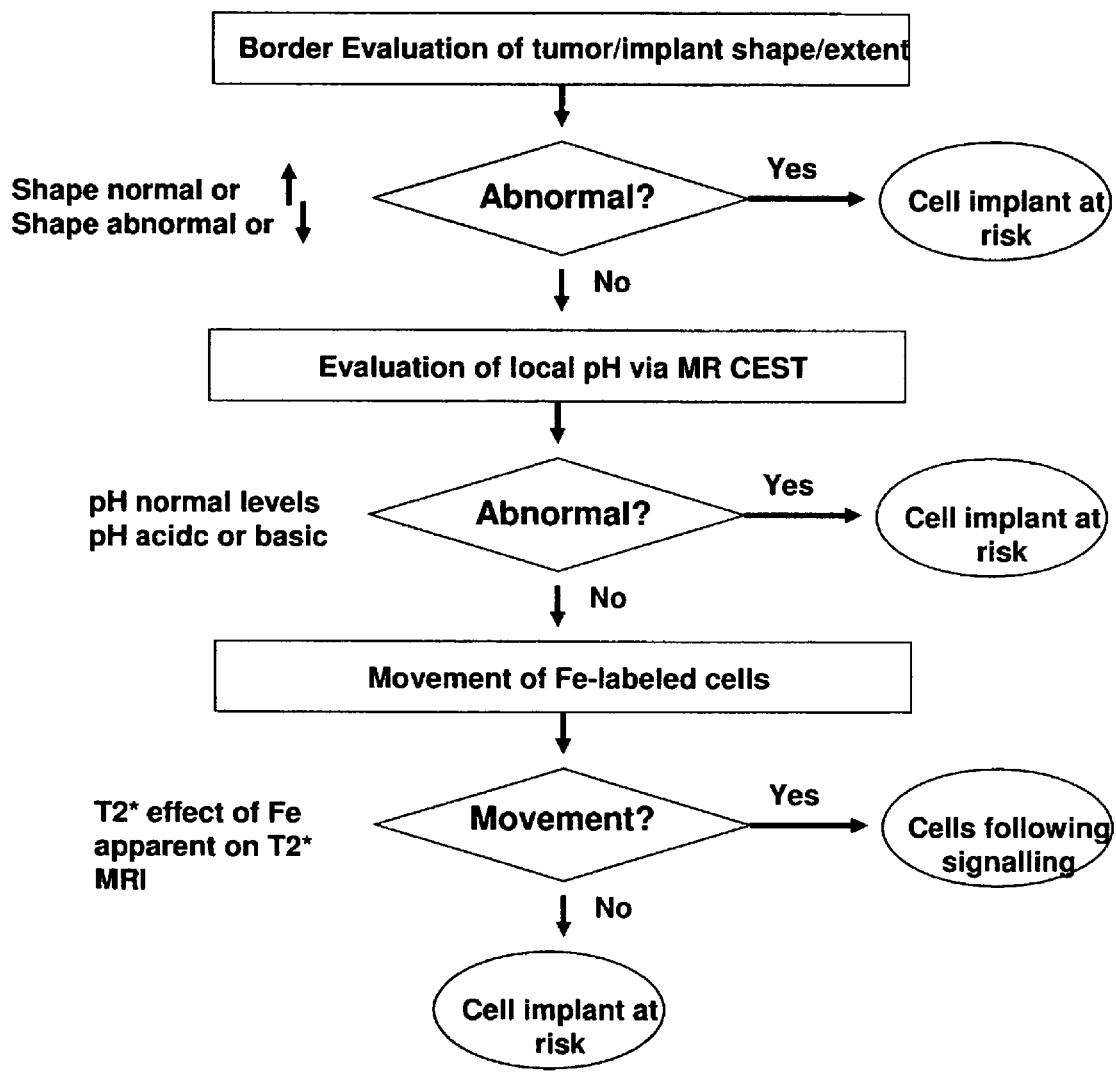
FIG. 1D is a flowchart of MRI visualization of blood flow with optical dyes.
Figure 2A:
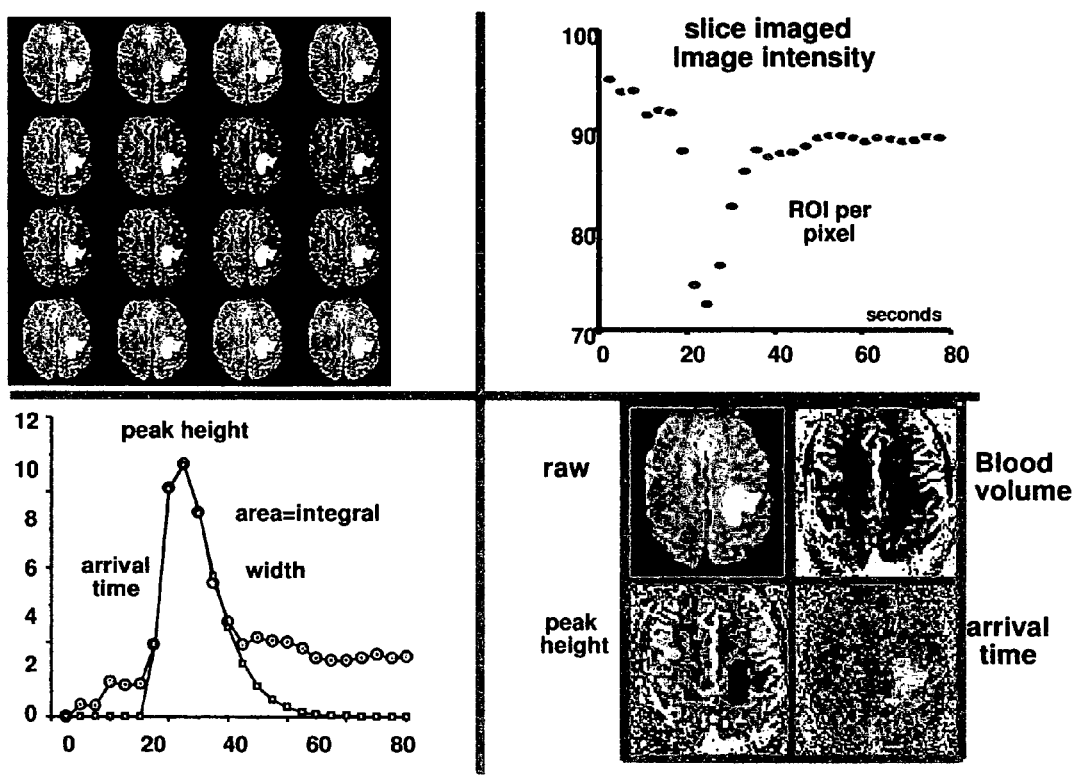
FIGS. 2A and 2B summarize the MR imaging and computational steps used according to the invention to evaluate blood flow and to calculate functional capillary perfusion density in the region of a population of normal implanted stem cells as well as in the region of a newly formed teratoma. The MR data enable a determination of the number of capillaries in an area or volume of tissue from which it is possible to approximate the average distance of any cell in a group of implanted stem cells to a functional (perfusing) capillary.
Figure 2B:
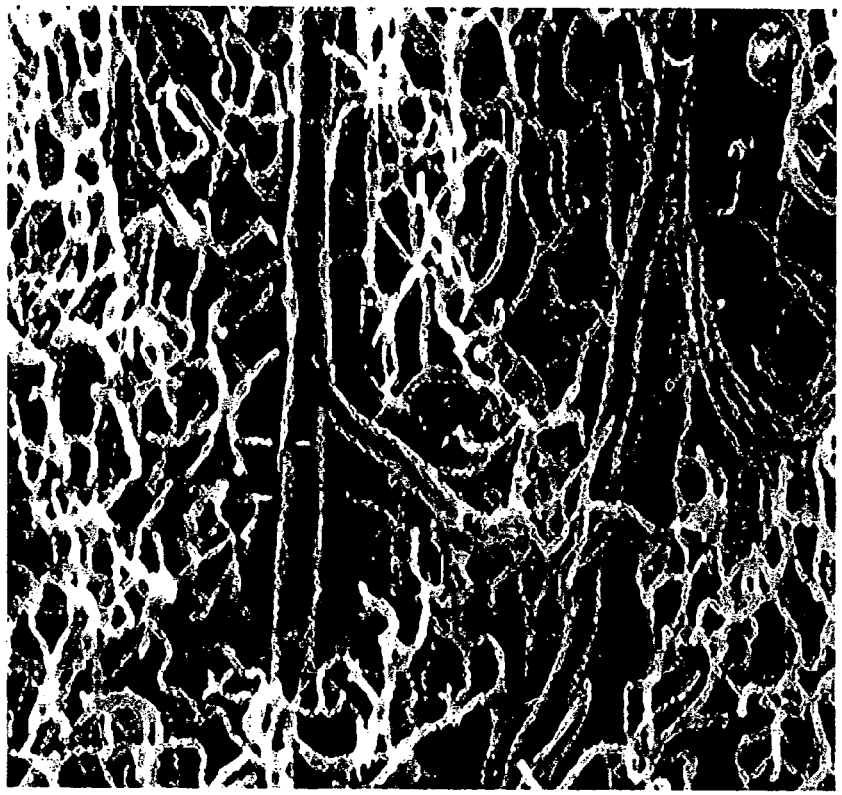
Figure 3:
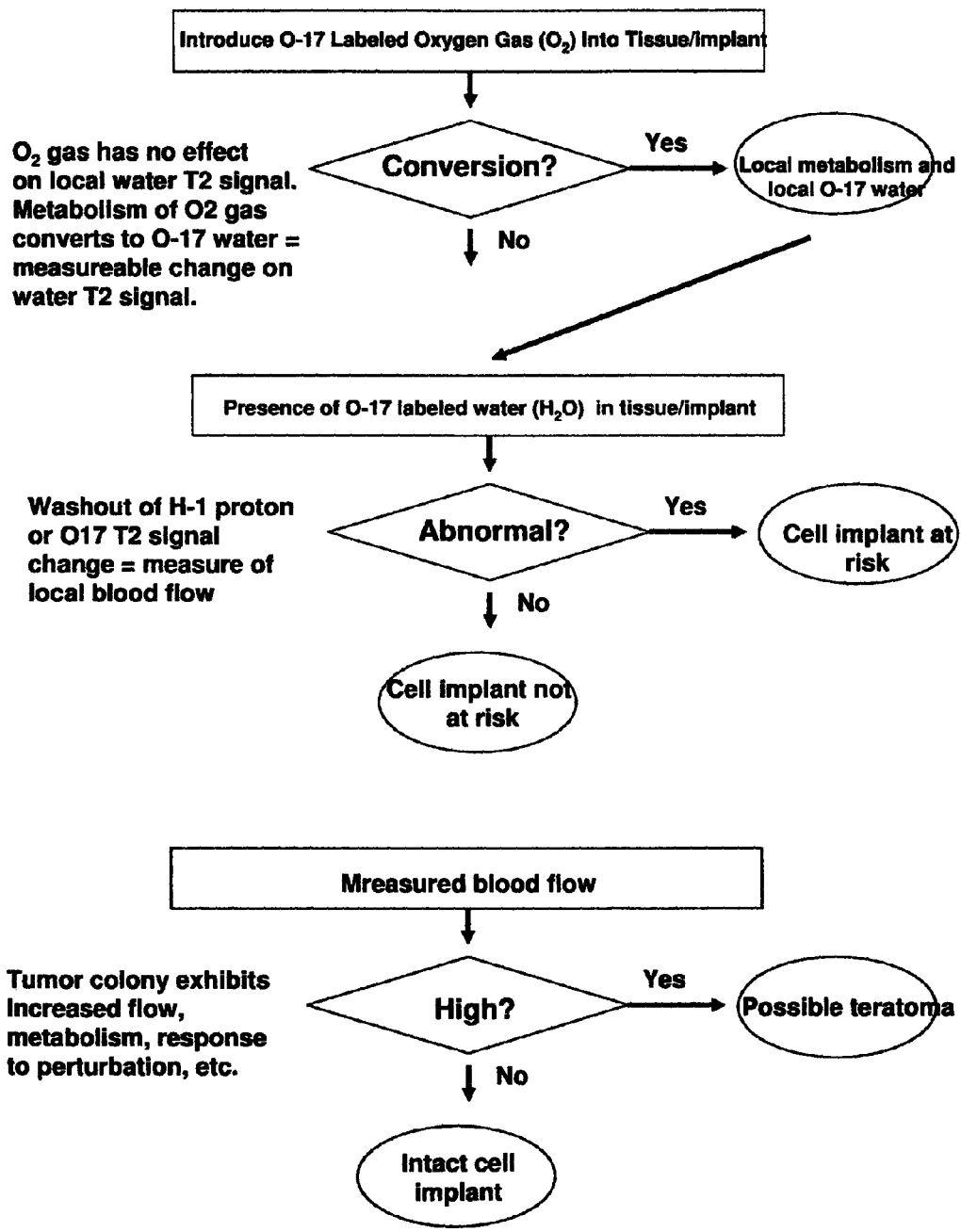
FIG. 3 is a flow chart that summarizes the MR imaging steps used according to the invention to evaluate perfusion and oxygen metabolism in a population of normal implanted stem cells and teratoma cells in contiguous tissue regions in vivo following the direct intracranial injection of $^{17}$O gas and labeled water.
Figure 4:
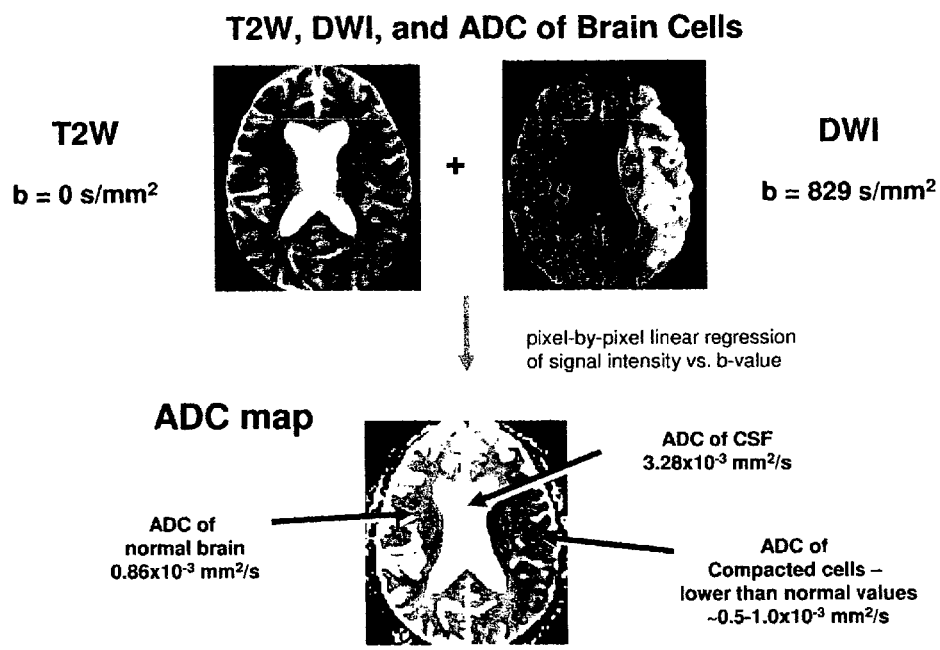
FIG. 4 is a compilation of how images are combined and summarizes the MR diffusion imaging steps used according to the invention to evaluate fluid-electrolyte homeostasis in a population of normal implanted stem cells and teratoma cells based on the ADC of the implant compared to the surrounding normal brain tissues.
Figure 5A:
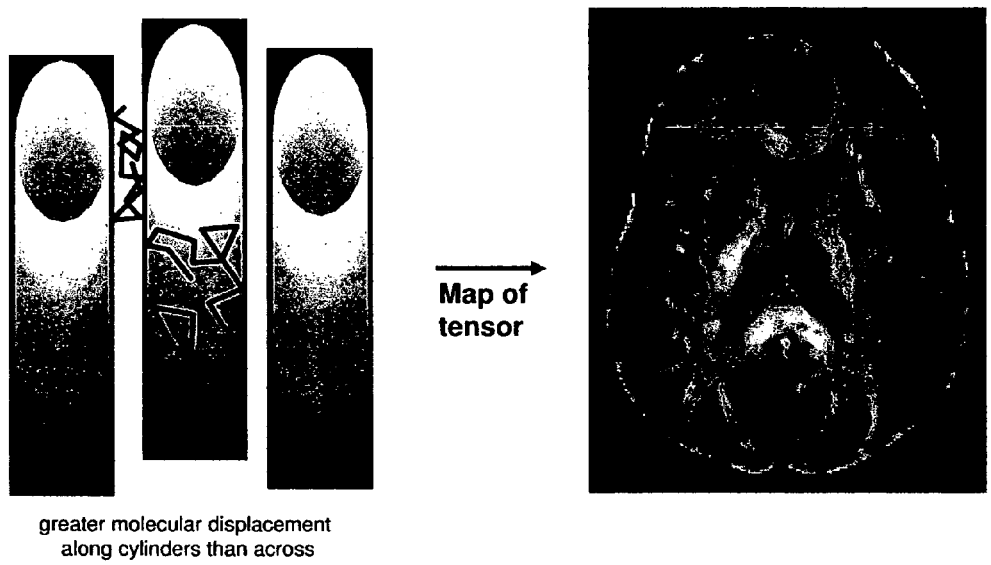
FIG. 5A summarizes the MR imaging steps used according to the invention to determine movement of Fe-labeled cells along white matter diffusion tensors.
Figure 5A:
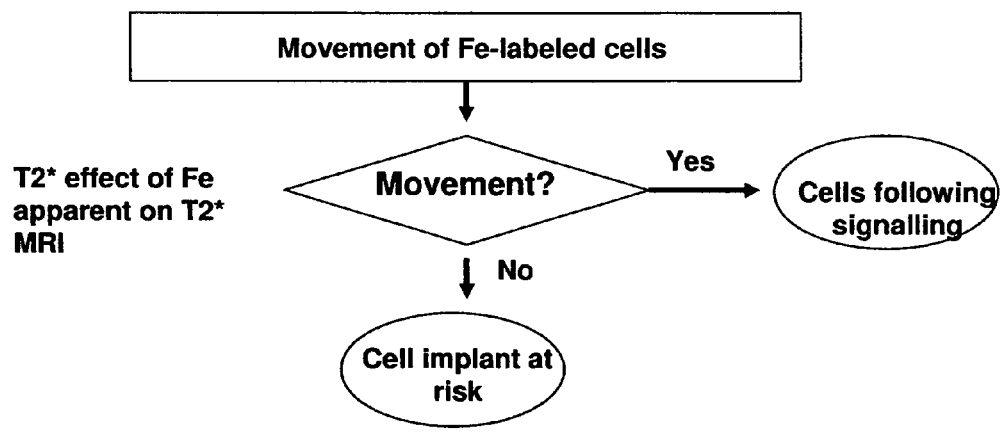
Figure 5B:
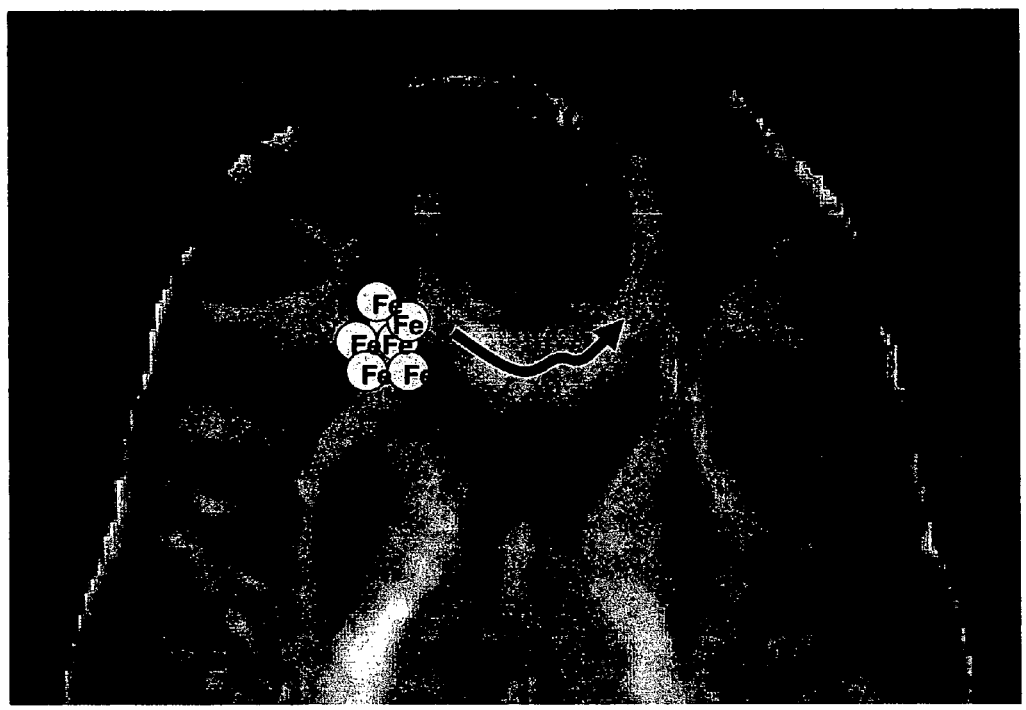
FIG. 5B shows a composite image estimating the movement of Fe-labeled cells along white matter diffusion tensors following signaling apparent frim T2 or T2*-weighted MRI.
Figure 6A:
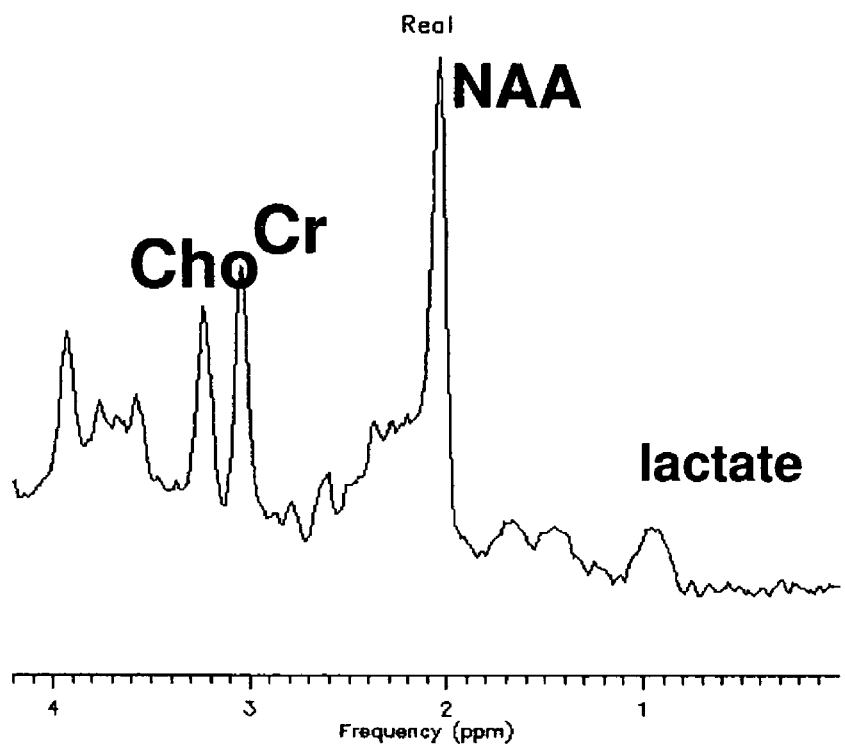
FIG. 6A illustrates a flow chart of MR spectroscopy for Local Metabolic Viability used according to the method of the invention to evaluate the general metabolic viability of normal implanted stem cells and abnormal teratoma cells. The metabolic changes are measured by MR using non-invasive in vivo proton spectroscopy with local or volume RF-coils, showing Cho, Cr, NAA and lactate peaks.
Figure 6B:
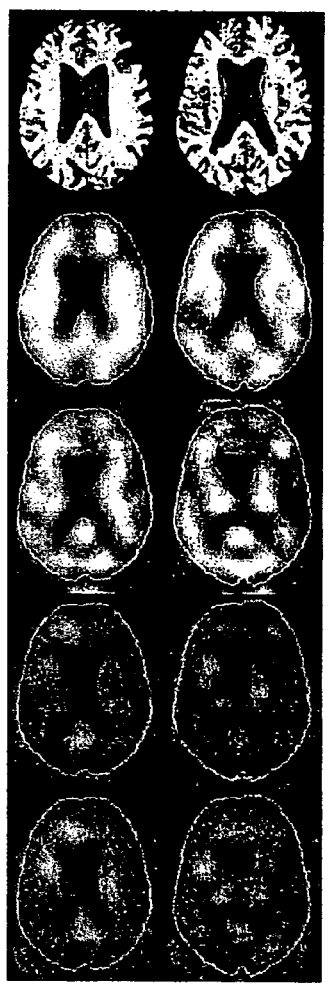
FIG. 6B shows MR Spectroscopic maps for five different image formats of a Segmented H-1 water image, Low-pass water image, N-acetyl image, Creatine image and Choline image.
Figure 6C:
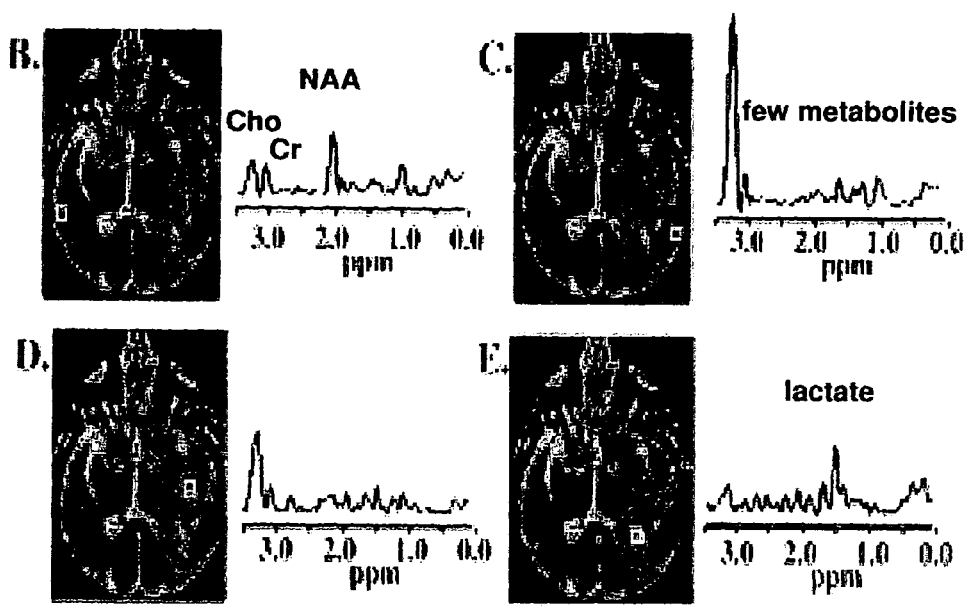
FIG. 6C shows four MR images evidencing Local Metabolic Viability and Metabolic Levels from Magnetic Resonance Scanning, and a flow chart for use of the information.
Figure 6C:
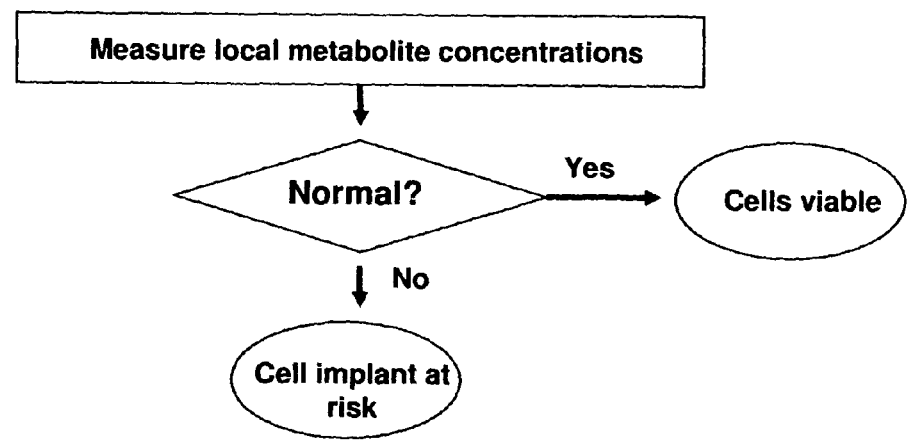

One adverse side-effect that can occur following stem cell implantation is the development of cell irregularities at the cell implant site. Stem cells implanted into the central nervous system for therapeutic purposes can sometimes transform into abnormal cells, including tumor cells (either malignant or benign), such as teratomas. An imaging means is needed for differentiating normal cell proliferation and angiogenesis following a cell implant from abnormal tumor growth and neovascularization associated with teratoma-inducing implanted stem cells.

Teratomas are the most common primary brain tumor seen in newborn children accounting for about 20% of germ cell tumors, and are more common in males. They tend to be found above the pituitary gland in the suprasellar region and in the pineal region. The tumors in the suprasellar region can present with visual problems and or developmental delay. The pineal region tumors can cause blockage of spinal fluid with hydrocephalus with presenting symptoms such as headache, nausea and vomiting. Hydrocephalus can also cause lethargy or coma. The definitive diagnosis of teratoma is usually based on MRI scanning performed without and with intravenous contrast enhancement. Treatment depends on the presentation. Hydrocephalus might require a shunt or a temporary external drain. Surgery to try to remove the tumor is an important step in treatment. Radiation therapy may be used after surgery. In children under the age of three years, chemotherapy might be used instead of radiation.

Teratoma formation that is associated with stem cell implantation is a significant indication of problems with the implant requiring immediate intervention. It is therefore desirable to provide a method for early detection of tumor development so that the earliest possible intervention may be practiced.

As with the detection of specific local chemical indicators that cell viability is not performing at expected levels (as described in U.S. patent application Ser. No. 09/606,137, filed Jun. 28, 2000, which reference is incorporated herein by reference), it has been found that the early stages of tumor growth associated with cell implantation can be determined by similar techniques. Local changes in cellular metabolic dysfunctions and abnormal local blood flow that are indicative of tumor formation can be detected. The use of this technology can be appreciated with respect to the specificity of tumor growth associated with cell implantation.

Cells are implanted in relatively specific areas at a specific time. Those specific areas can therefore be easily identified for tracking according to the observation methods of the invention. The medical practice does not have to attempt the nearly impossible task of monitoring the entire body, but on those areas where the implantation has been attempted. Even after initial success has been observed based on monitoring cell survival, the present invention allows for additional monitoring of the region to ascertain whether there are chemical indications (as opposed to visual observation of microscopic growths or even macroscopic growths of tumor). The practitioner monitors the region of the implant for specific chemical changes that are observable by non-invasive imaging, those specific chemical changes identifying tumor growth or initial tumor appearance at the region of the implant.

Specific biochemical alterations that may be noted in the area or region of the implantation that could be indicative of tumor development include, but are not limited to increases or decreases in specific chemical content or concentration that is the result of the reaction of tumor cells with naturally provided or artificially provided chemistry to the region, an increase in specific chemical content or concentration that is the result of the decomposition reactions or growth reactions of tumor cells, and the like.

Blood flow and oxygenation are critical factors controlling the physiological microenvironment within tumors and, directly or indirectly, are also major determinants of the outcome of nonsurgical forms of cancer therapy. One of the main pathophysiological characteristics of tumor blood flow is its heterogeneity, which is reflected in a heterogeneous oxygen, pH, and metabolite distribution. Necrosis, either due to limitation of blood flow and substrates or to actual vascular collapse, is also frequently observed. A large volume of data indicates that blood flow and oxygenation are important factors governing both the growth of tumors and their response to therapy. Poor blood flow can impair the delivery of chemotherapeutic agents, and the effective of hyperthermia therapy.

MRI methods have been used to investigate the relationship of tumor metabolism to blood flow and oxygenation, proliferation, and differentiation. Several reviews published in the medical literature ( eg. Wehrle and Glickson, Cancer Biochem Biophys 1986, 8: 157-166; Negendank, NMR Biomed 1992, 5: 303-324; Howe et al., Magn Reson Q 1993, 9:31-59) have summarized the morphological, metabolic, and physiological characteristics of tumors and their relationship to H1, C13, and P31 measurements obtained by MR spectroscopy.

Tumor growth to a volume of about 1 cubic mm can be accomplished without contiguous microvascular support, since all the essential nutrients and waste products can diffuse across this distance. However, blood vessels are essential for tumor progression. Inadequate local blood flow and low concentrations of glucose and oxygen appear to influence the latency of expression of DNA damage. Blood flow also controls cellular environment and heat clearance, factors which are important in hyperthermia treatment of tumors. The sensitivity of cells to radiation depends significantly on the concentration of cellular oxygen. A non-invasive method of monitoring blood flow and oxygenation, in conjunction with methods to modify these parameters, would increase the effectiveness of early detection of tumors and potentially improve treatment strategies during the early stages of tumor development.

Tumor vascular supply is derived from normal vessels incorporated from the host tissue and new blood vessels stimulated by tumor angiogenesis factors (Folkman and Klagsbum, Science 1987, 235:442-447). Neovascular development is characterized by various structural abnormalities, including an absence of smooth muscle cells, collapsed vessels due to increased tissue pressure, stasis, large sinusoidal structures, arteriovenous shunts, and thrombosis (Jain, Cancer Res 1988, 48:2641-2658).

If neovascularization associated with new tumors cannot match the rapid proliferation of tumor cells, the result is reduced and inhomogeneous supply of blood, substrates, and oxygen leading to hypoxia, anoxia, and ultimately tumor cell death. Surviving cells generally are located at distances of 150 microns or less from the nearest blood vessel (Thomlinson and Gray, Br J Cancer 1955, 9:539-549). However, cellular debris, fatty acids, proteins, and nucleic acid fragments present in necrotic areas can also interfere with mitochondrial functioning of cells in adjacent perfused areas (Falk, Eur J Cancer Clin Oncol, 1992, 18:155-165). The composition of tumor interstitial fluid is similar to normal interstitial fluid, except for high concentrations of lactate (10-30 mM), and a very low content of free glucose (0-2 mM). Tumors also have elevated interstitial pressure, which has been attributed to the absence of functioning lymphatics, the high filtration coefficient and vascular permeability of tumor blood vessels, and the rapid proliferation of cells in confined spaces (Less et al., Cancer Res., 1992, 52:6371-6374).

By comparison with other methods, MR is capable of measuring blood flow and oxygenation non-invasively, either indirectly by evaluating metabolism or by using contrast agents. H1 MR spectra of brain tumors show increased lactate and total choline and reduced N-acetyl aspartate (NAA) levels compared to normal brain spectra (Negerdank, NMR Biomed, 1992, 5:303-324). The high levels of lactate are consistent with high glycolytic rates and poor blood flow associated with tumors. The high levels of total choline may be due to increased membrane degradation or turnover, since the choline compounds observed in Hi MR spectra are both membrane precursors and breakdown products. Hypoxia is known to result in membrane breakdown and the release of free fatty acids.

In addition to abnormalities of metabolism, tumors in general are characterized by neovascularization and increased angiogenic activity, as well as apoptotic death or damage to endothelial cells. It is also known that, as a consequence of these physiologic mechanisms, tumors may have a higher proportion of immature or defective, and thus hyperpermeable, vessels, and particularly in the brain are associated with different degrees of damage to the blood brain barrier (BBB).

Contrast enhancement of the brain using intravenous small-molecular, Gd-based contrast agents as typically observed on clinical magnetic resonance images is the result of a combination of the vascularity of a tissue, i.e. the fractional blood volume (fBV) and the accumulation of the contrast agent in the tissue interstitium, consequent to transendothelial diffusion (microvascular permeability). The rate of such transendothelial contrast medium diffusion is a reflection of the integrity of the microvessel endothelial barrier, or, specifically in the brain, the blood brain barrier.

There are several approaches to non-invasively image the two sequelae of angiogenesis, the increase in vascularity, i.e. the higher blood volume, and the microvascular hyperpermeability. Most commonly used are first pass techniques, based on the magnetic susceptibility contrast phenomenon and the resulting changes in $T2^*$. $T2^*$-methods have certain disadvantages. They require implementation on high-field magnets using preferably echo-planar or, with lower spatial or temporal resolution, gradient-echo sequences. Without a reference blood signal, only relative CBV values can be obtained. Even with more sophisticated analyses including arterial input fuction, CBV determinations remain approximate. The anatomic coverage is typically limited, and there is sensitivity to susceptibility artifacts near large vessels or osseous structures, which, for example, makes it difficult to assess infratentorial tumors.

An alternative method is based on T1 changes after contrast agent administration. This does not assess the first pass of the contrast agent but rather its distribution within the first few minutes after injection, i.e. the equilibrium phase. In general, dynamic, contrast-enhanced imaging is used to draw regions of interest in the tissue of interest (whole tumor or certain tumor regions such as center or rim) and a reference blood vessel,. This analysis yields estimates of fractional tissue blood volume (fBV[ml/cc]) and microvascular permeability, expressed as the transendothelial transfer constant k [ml/100 cc*min]. Furthermore, using a more simplified kinetic model, synthesized spatial maps of estimates of fBV and k can be created.

This technique for the quantification of fBV and microvascular permeability has been established in numerous animal models. Dynamic, contrast-enhanced MR with a macromolecular contrast agent can be used to quantify microvascular permeability in tumors, which increases with increasing tumor malignancy. It has also been shown in a human breast tumor model that permeability reduction determined from MR in response to anti-angiogenic pharmaceutical therapy correlates with decreased tumor growth rate. It has been further demonstrated in a human brain tumor model in athymic rats that dynamic MR with Gd-DTPA can be analyzed similarly to quantify blood volume and microvascular permeability and to quantitatively monitor anti-angiogenic therapy.

It is also to be noted that one aspect of the present invention is the observation of these changes within tissues. By observing rates of intracellular transfer in an area, normal cells, viable cells, deteriorating/dying cells, and tumor cells can be differentiated and detected, and even possibly quantified. Although identification of tumor cell appearance and growth may be assumed to be more important that quantification of tumor cell growth, the latter can be significant to the medical observer.

It is also to be noted that tumor growth is less likely to be an effect immediately attendant with or accompanying initial cell implantation, and that monitoring is more likely to be important significant time periods (days, weeks, months and even years) after any initial or subsequent implantation of cells. Therefore, such tumor chemistry detection is most likely to be performed as a separate operation event from initial cell implantation, although it may be performed when and if secondary or subsequent cell implantation occurs.

In the method of the present invention, MRI navigation procedures are used to guide an MR-compatible access device and a catheter containing the cell implant to a target location in the brain or other tissue. Following MRI-guided positioning of the catheter tip at the target location, delivery of the cell implant is monitored using high-resolution MR imaging in combination with optical or other imaging methods. Further in the method of the invention, high-resolution MRI methods are used to non-invasively evaluate the viability of implanted cells.

According to the present invention, MRI navigation procedures are used to guide an MR-compatible intracranial access device, such as described in U.S. Pat. No. 6,061,587 to Kucharczyk and Moseley, which is used in combination with a specialized catheter, such as disclosed in U.S. Pat. No. 6,599,274 and U.S. patent Ser. No. 10/444,884 to Kucharczyk et al., containing the cell implant to reach a target location in the tissue. Following MRI-guided positioning of the catheter tip at the target location, delivery of the cell implant is monitored using high-resolution MRI as disclosed in U.S. Ser. No. 09/606,137 to Moseley and Kucharczyk and U.S. patent Ser. No. 09/866,524 to Raghavan et al. According to the present invention, delivery of therapeutic agents such as cells and drugs may also be performed by infusion via convection efflux from a single peripheral lumen, or via a multi-port and/or multi-lumen configuration, such as disclosed in U.S. Pat. No. 6,599,274 to Kucharczyk et al. or U.S. Pat. No. 6,626,902 to Kucharczyk et al., in order to facilitate broad spatial distribution of the drug within the region of the cell implant. Each and every one of these references and all patents referred to herein are incorporated by reference for support and enablement of the presently described technology.

In the method of the invention, the cells may include secretory cells which have been isolated from natural sources, or have been genetically engineered to produce neuroactive factors, growth factors, cytokines, antibodies, extracellular matrix components or neurohormonal agonists (peptides or bioactive amines), precursors, active analogs, or active fragments. In a preferred aspect of the invention, the cell is an allograft or a xenograft. Preferred cell types may include all types of precursor or differentiated stem cells. Any cells that have been genetically engineered to express a neurotransmitter or its agonist, precursor, derivative, analog, or fragment which has similar neurotransmitter activity, or bioactive macromolecular factors, can also be used to practice this invention. For example, genetically engineered fibroblasts or other cell types may be used.

As used herein, the term "biologically active factors" has the same common meaning as described in U.S. Pat. No. 5,487,739, namely, neurotransmitters, neuroactive analgesic factors, as well as precursors, agonists, active analogs, and active fragments. Also included are proteins, nucleic acids and other macromolecules having biologic activity, as well as agents which might be infused for their physical or chemical properties. Examples of biologically active macromolecules could include growth factors, cytokines, antibodies, hormones, oligonucleotides, modified long DNA constructs (synthetic vectors), glycoproteins and glycolipids. Examples of agents which might be infused for their physical properties could include radiographic contrast agents or reagents to enhance the in vivo detection of implanted cells or the products they have been engineered to produce. Also expressly included are cells that secrete neuroactive factors and hormones, including "growth factors" such as described in U.S. Pat. No. 5,487,739 to Aebischer et al.

Viewed from one aspect, the present invention provides MR imaging methods for evaluating the viability of a cell implant over days, weeks, or months. In the method of the invention, high-resolution MRI methods, most preferably diffusion imaging, as disclosed in U.S. Pat. Nos. 6,026,316 and 6,061,587, co-authored by the present inventors, can be used to evaluate the viability of the cell implant and to evaluate fluid-electrolyte homeostasis in the extra- and intra-cellular fluids contiguous with the cell implant.

According to the methods of the invention, cell viability may be assessed by monitoring the presence of anisotropic water diffusion. As the implanted cells organize into coherent patterns or populations, orientational influences are imposed on the mobility of adjacent water protons giving rise to fractional anisotropy changes that can be measured with MR. Further in the method of the invention, cell viability may also be assessed by monitoring the increases in local tissue density by measuring the water proton diffusion in the local tissue. As the cells grow and proliferate, the local density will increase, the local water content will decrease, and the water diffusion coefficient measured by diffusion-weighted MRI will decrease. Thus, according to the invention, cell viability can be assessed by measuring the apparent diffusion coefficient of the ADC by non-invasive proton diffusion MRI.

According to the invention, the viability of implanted cells may also be assessed by measuring the evolution of certain MR-visible metabolites needed for cell replication. These metabolites include choline, N-acetylaspartate (NAA) and gaba-aminobutyric acid (GABA). In one embodiment of the invention, the local concentrations of choline, NAA, GABA, phosphocholine, creatine are measured from volume MRI RF-coils surrounding the tissue or from the introduction of local MRI RF-coils. Metabolite signals are observed from non-invasive proton spectroscopy or from localized proton spectroscopic imaging.

In another embodiment of the invention, cell viability is assessed by measuring changes in the local hemoglobin oxygenation state together with changes in the local $T2^*$ reflecting the alterations in tissue oxygenation. Cell proliferation will increase local metabolism, thereby increasing local vascular autoregulation, and preferentially delivering fully oxygenated arterial blood, which will in turn increase the local $T2^*$. In the method of the invention, the increased delivery of oxygenated blood can be monitored by monitoring the local $T2^*$ changes from volume MRI RF-coils outside the tissue or by local MRI RF-coils introduced by image-guided catheters.

In the method of the invention, cell viability may also be assessed by measuring changes in the vascular reserve and response to oxygenation stresses. As the population of cells in the cell implant region grows over time, the local microvasculature will develop increasing numbers of arterioles which are sensitive to local carbon dioxide concentrations. According to the invention, if the $CO_2$ is increased by infusion of an exogenous gas or by an oxygenation stress (such as breath-holding or hypoxia or hypercapnia), local vascular autoregulation can be assessed by blood flow or perfusion MRI, by $T2^*$ imaging or by changes in local lactate or metabolic activities.

Viewed from another perspective, the invention provides a method to evaluate the functional capillary density of the cell implant longitudinally over days, weeks, and months to confirm that the cell implant has adequate perfusion to sustain its viability and growth. In the method of the invention, MR first-pass perfusion imaging, such as disclosed by U.S Pat. Nos. 5,190,744, 5,494,655, and 5,833,947 to Rocklage et al. are used to measure perfusion in the volume of brain tissue occupied by the cell implant in ml/gram tissue/minute. The average distance of any cell in the implant to a functional perfusing capillary can be estimated by knowing the number of cells implanted and the volume of the cell implant. The functional capillary density can then be expressed as the number of perfusing capillaries per 1000 cells/per minute. Deficiencies in perfusion can be established by measuring a low functional capillary density, whereupon the implant can be treated by the local intracranial administration of angiogenic or other neurotrophic drug agents to improve perfusion and long-term cell viability.

According to the invention, the operational utility of 'functional capillary density' is best approximated in terms of an estimated number of active perfusing capillaries in a unit volume of the tumor compared with normal tissues contiguous with the tumor. MR first-pass perfusion imaging can initially be used to measure perfusion in a known volume of normal and abnormal tissues in ml/gram tissue/minute. The average distance of any cell in each volume to a functional perfusing capillary can be estimated by knowing the number of cells in the volumes of normal and abnormal tissues. Estimates of cell density in normal and tumor tissues will be obtained from the neuroanatomy and neuropathology literature. For instance, if GBM cells are on the order of 10 µm in mean diameter, then the hypoxic core of the tumor will have approximately $10^8$ cells per cc tissue, whereas astrocytoma Stage 1 tumors will have a smaller cell density, with the exact value depending on the packing fraction and other biophysical parameters; see Wein, L. M., et al., "Dynamic Optimization of a Linear Quadratic Model with Incomplete Repair and Volume-Dependent Sensitivity and Repopulation," International Journal of Radiation Oncology and Biological Physics, 47(4), 1073-1083, (2000). Similarly, cell size and density in various brain nuclei are already described in the published neuroanatomy literature.

The functional capillary density can then be expressed as the number of perfusing capillaries per 1000 cells/per minute. The average distance of any tumor cell or normal cell to a functional (perfusing) capillary can then be estimated. Brain tumors are expected to demonstrate greater 'functional' vascularity (functional capillary density) than normal brain tissue. In the method of the invention, 3D MR images acquired before bolus injection of T2* contrast agent followed by enhanced 3D images after contrast injection can be spatially and temporally resolved and registered, then subtracted to remove ambient noise and to highlight abnormal signal voxels. Areas of tumor can be identified by connecting contiguous regions of abnormal signal intensity. Areas of proliferating (malignant) tumor (significantly increased functional capillary density) can be identified by determining the ratio of volume to surface area which falls below a certain threshold.

U.S. Pat. No. 6,491,894 to Ruoslahti et al. provides a method of identifying a tumor homing molecule that homes to angiogenic vasculature by contacting a substantially purified NGR receptor with one or more molecules and determining specific binding of a molecule to the NGR receptor. The invention also provides a method of directing a moiety to angiogenic vasculature in a subject by administering to the subject a conjugate including a moiety linked to a tumor homing molecule that exhibits specific binding to an NGR receptor, whereby the moiety is directed to angiogenic vasculature. In addition, the invention provides a method of imaging the angiogenic vasculature of a tumor in a subject by administering to the subject a conjugate having a detectable moiety linked to a tumor homing molecule that exhibits specific binding to an NGR receptor and detecting the conjugate.

U.S. Pat. No. 6,112,112 to Gilhuijs et al. provides a method and computer program product for the assessment of tumor extent in MR images. The method, on which the computer program product and system is based, includes obtaining image data corresponding to temporally acquired images including a tumor and surrounding anatomy and performing variance processing on the obtained image data to derive variance image data defining a variance image indicative of variation of voxels in the temporally acquired medical images. Techniques include novel developments and implementations of breast volume segmentation, breast border removal, lesion enhancement, determination of the bounding sphere, computation of a 3-D search volume, suppression of surrounding structures, and volume growing. Output from the methods yields an estimate of the extent of the tumor (lesion) in the breast.

U.S. Pat. No. 6,310,477 to Schneider discloses an MR means for evaluating tumors based on acquiring a 3D MR image before injection of a contrast agent and an enhanced 3D image after injection of the contrast agent. The two images are registered and then subtracted to remove background and to highlight lesion voxels. Lesion objects are identified by connecting contiguous lesion objects. Volume and surface area of any continuous lesion object in a discrete digital image are then calculated. Malignant lesions are identified by determining the ratio of volume to surface area for each lesion object. Malignant tumors are identified when this ratio drops below a preset threshold.

Functional capillary density of normal versus tumor tissues may also be assessed by measuring changes in the vascular reserve and response to oxygenation stresses in the tissues. As the population of abnormal cells in a malignant tumor grows over time, the local microvasculature will develop increasing numbers of arterioles which are sensitive to local carbon dioxide concentrations. If the $CO_2$ is increased by infusion of an exogenous gas or by an oxygenation stress (such as breath-holding or hypoxia or hypercapnia), local vascular autoregulation can be assessed by blood flow or perfusion MRI, by T2* imaging or by changes in local lactate or metabolic activities. Cell viability can be assessed by measuring changes in the local hemoglobin oxygenation state together with changes in the local T2* reflecting the alterations in tissue oxygenation. Cell proliferation will increase local metabolism, thereby increasing local vascular autoregulation, and preferentially delivering fully oxygenated arterial blood, which will in turn increase the local T2*. The increased delivery of oxygenated blood can be monitored by observing the local T2* changes from volume MRI RF-coils outside the tissue or by local MRI RF-coils introduced by image-guided catheters.

Apart from the anticipated higher capillary density characterizing tumors compared to normal tissue, malignant tumors also have blood vessels that behave differently from capillaries in normal brain tissue in response to vasoactive drug agents. For example, the vasodilator hydralazine can be used to reduce tumor blood flow in tumors based on the "steal" phenomenon; see Jirtle, R. L., "Chemical Modification of Tumor Blood Flow," International Journal of Hyperthermia, 4(4), 355-371 (July-August 1988). The decrease in systemic blood pressure and the vasodilatory action of hydralazine on the arteriolar smooth muscle cells, present in normal tissue vasculature, but absent in poorly differentiated tumor vasculature, results in near vascular collapse within the tumor. $^1$H MR spectra obtained following administration of hydralazine will show a predictable increase in the lactate peak in the tumor area related to tumor size (number of tumor cells) with no changes in total choline or creatine. These changes are consistent with the glycolytic metabolism of glucose to lactate to maintain energy levels in the absence of oxygen.

Viewed from another perspective, the present invention also provides a method to measure perfusion and oxygen metabolism of the cell implant in vivo by using $^{17}$O gas and labeled water. $H_2^{17}O$ is a freely diffusible tracer which has been used for in vivo blood flow measurements. While $H_2^{17}O$ has several disadvantages, including low sensitivity of $^{17}$O NMR, low natural abundance of $H_2^{17}O$ (0.035%), and high cost of $^{17}$O enriched compounds, publications in the medical literature, eg., Kwong, K. K., et al., "Proton NMR Imaging of Cerebral Blood-flow Using $(H_2O)$—$^{17}$O," Magnetic Resonance in Medicine, 22(1), 154-158, (November 1991); Hopkins, A. L., et al., "Improved Sensitivity of Proton MR to $^{17}O$ as a Contrast Agent Using Fast Imaging,—Detection in Brain," Magnetic Resonance in Medicine, 7(2), 222-229, (June 1988), have reported improved sensitivity of $H_2^{17}O$ in imaging applications using the $T_2$-relaxation effect of $H_2^{17}O$ on protons at steady state concentration and as a bolus injection for CBF measurement. $^{17}O$ shortens proton $T_2$ via an exchange modulated scalar coupling through the hydrogen bond; this interaction can be suppressed by irradiating at the $^{17}O$ frequency (i.e. decoupling) while protons are undergoing T2 relaxation. This effect has previously been exploited to measure $^{17}O$ concentration by comparing the $^1H$ signal in a spin-echo sequence with or without $^{17}O$ decoupling, eg., Ronen, I., et al., "A New Method for Proton Detection of ($H_2O$)—$^{17}O$ with Potential Applications to Functional MRI," Magnetic Resonance in Medicine, 32(6), 789-793, (December 1994) and for MR imaging using a double tuned coil, eg., Reddy, R., et al., "$^{17}O$-Decoupled $^1H$ Detection Using a Double-Tuned coil," Magnetic Resonance Imaging, 14(9), 1073-1078, (1996).

In the method of the invention, $^{17}O_2$ gas is introduced into tissues of the brain contiguous to the cell implant in order to evaluate the metabolic state by monitoring the conversion of the gas to $H_2^{17}O$ water, which then shortens the water proton T2 values. The extent of T2 shortening reflects the metabolic state of the tissue, and can be measured by MR, according to the methods of the invention.

This embodiment of the method of the invention will now be described further by way of example with particular reference to certain nonlimiting embodiments, in this case an experimental study in which 1000 embryonic stem cells were implanted into the basal ganglia of young male rats. A femoral vein catheter was inserted for contrast agent injection. MR imaging was carried out using a 2T GE Omega system. A 25 mm $^1H$ surface coil was placed on the rat's head, with an orthogonal $^{17}O$ Helmholz coil around it. Coil isolation was improved with proton bandpass/reject filters in the $^1H/^{17}O$ coil cables. Multislice $T_2$-weighted EPI (FOV 40 mm, 64×64, 1.5 mm slice, TE 90 ms) was used. Three axial slices covered the rat brain, while one slice covered tubes of 0.4% atm. and 0.9% atm. $H_2^{17}O$ used as standards. Dynamic $T_2$ EPI (TR 2s) was performed during a bolus injection of 1.0 ml of 10% atm. enriched $H_2^{17}O$ into the femoral vein. Five minutes later, a series of 128 $T_2$-wt. images was acquired (TR 4s) with the decoupler alternately switched on and off every 16 images. Decoupler power was applied either side of the 180° pulse. For each pixel, the cross correlation coefficient was calculated between the signal and the 'on-off-on' decoupler time course and correlation maps were generated. Pixels with high enough $H_2^{17}O$ concentration will yield a significant correlation. Diffusion EPI and perfusion imaging of a GdDTPA bolus were also carried out.

Increases in ICP induced by a teratoma tumor formed from implanted stem cells can injure tissues directly (by pressure-induced cell membrane perturbations), or indirectly (by retarded interstitial solute transport). Thus, it is advantageous to monitor any local and regional increases in ICP resulting from injections of liquid drug agents directly into the brain parenchyma. U.S. Pat. No. 6,537,232, co-authored by one of the present inventors, discloses an MR-visible delivery device which incorporates a method and means for monitoring ICP, and to obtain near real-time information on tissue pressure changes during interventional procedures in an intra-operative MR system.

In the method of the present invention, a feedback mechanism is used to automate and optimize the monitoring of cell viability, wherein a number of physiological variables can be taken into account by the algorithm that governs the therapeutic response of the catheter system. In a preferred embodiment, physiological and metabolic data on the status of the patient (derived form other sensors on/in the body, such as, for example, probes or apparatuses which monitor tissue oxygen levels, blood flow, and other physiologic parameters) can be incorporated into the algorithm's treatment optimization process.

In a preferred embodiment of the method of the invention, the algorithm governing the patient's therapy preferably utilizes proportional-integral-derivative (PID) control functions, adaptive control functions, nonlinear control functions, multi-variable/state-space control functions, stochastic control functions and/or any other functional approach deemed appropriate for the implementation of the therapy. In all such cases, the controller could be designed to respond to changes in the patient's condition using artificial intelligence or other cybernetic techniques that would let the feedback mechanism "learn" the best way to respond to changes in the patient's physiological or anatomical status. Such techniques might employ, among other techniques, "fuzzy logic" algorithms that can function in the presence of incomplete or indeterminate data.

In the preceding detailed description of the preferred embodiments, reference is made to the accompanying drawings which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that structural, logical, physical, computational, medical, architectural, and electrical changes may be made without departing from the spirit and scope of the present invention. The preceding detailed description is, therefore, not to be taken in a limiting sense, and the scope of the present invention is defined only by the appended claims and their equivalents.

We claim:

1. A method for providing an indirect indication to a medical observer of tumor cells in a region where cell implantation has occurred comprising:
   implanting cells into a region of a patient;
   observing with magnetic resonance imaging or spectroscopy methods in that region of a patient into which cells have been previously implanted;
   detecting with the magnetic resonance imaging or spectroscopy methods a quantitative change in chemical content or chemical concentration in the region of the cell implant; and
   identifying from the quantitative change quantitative magnetic resonance indicators that are diagnostic for the presence of tumor cells in advance of being able to visualize a tumor with clinical magnetic resonance imaging.

2. The method of claim 1 wherein there is a quantitative magnetic resonance indicator of implanted cells that comprises measuring quantitative changes in content or in concentration of chemicals attached to at least one receptor on a tumor cell.

3. The method of claim 1 wherein there is a magnetic resonance indicator that indicates a chemical reaction between locally introduced chemistry and by-products of tumor cell metabolism.

4. The method of claim 1 wherein there is a quantitative magnetic resonance indicator that responds to quantitative measuring of quantitative changes in observable proton observable metabolites selected from the group consisting of GABA, PCr and ATP.

5. The method of claim 1 wherein there is a quantitative magnetic resonance indicator that is used in measuring a quantitative change in tissue sodium using $^{23}$Na MRI 6. The method of claim 1 wherein there is a quantitative magnetic resonance quantitative indicator that provides signals based upon a quantitative relationship between the predicted number of cells in the cell implant that have been transformed to tumor cells, acute changes in regional blood flow induced by administration of vasoactive stressor drugs, and increases in regional lactate levels measured by $^1$H magnetic resonance.

7. The method of claim 1 wherein there is a quantitative magnetic resonance indicator that provides a response in the region that is based upon measurements of quantitative, localized phosphorous high-energy metabolite concentrations by non-invasive in vivo $^{31}$P MR spectroscopy.

8. The method of claim 1 wherein there is a magnetic resonance indicator that provides a response to local tissue blood flow that is monitored by at least one process selected from the group consisting of a) MR perfusion imaging following infusion of T1- or T2*-shortening agents selected from the group consisting of MR-visible paramagnetic, superparamagnetic, and non-magnetic contrast agents; b) the local introduction of hyperpolarized Xenon gas using identification of elimination of the Xe and the decay of the Xe signal; and the use of optically-active dyes and coloring agents by monitoring concentration-time changes in the dyes or coloring agents by an optical probe.

9. The method of claim 1 wherein measuring alterations in tissue sodium by $^{23}$Na MRI is based on chemical shift differences from introduced chemical shift reagents to separate the extracellular from the intracellular sodium.

10. The method of claim 1 wherein said cell implantation comprises a surgical implant of stem cells.

11. The method of claim 1 wherein said tumor cells comprise early stage teratoma cells in advance of microscopically visually observable cells.

12. The method of claim 1 wherein said cell implantation comprises a surgical implant of embryonic stem cells.

\* \* \* \* \*